United States Patent [19]

VandenBerg

[11] Patent Number: Plant 7,616

[45] Date of Patent: Aug. 6, 1991

[54] CHRYSANTHEMUM PLANT NAMED DARK OREO

[75] Inventor: Cornelis P. VandenBerg, Salinas, Calif.

[73] Assignee: Yoder Brothers, Inc., Barberton, Ohio

[21] Appl. No.: 435,822

[22] Filed: Nov. 14, 1989

[51] Int. Cl.[5] ..... A01H 5/00

[52] U.S. Cl. ..... Plt./74

[58] Field of Search ..... Plt./74, 76; 47/58; 800/200

[56] References Cited

U.S. PATENT DOCUMENTS

P.P. 6,882 6/1989 VandenBerg ..... Plt./74

4,616,099 10/1986 Sparkes ..... 47/58

OTHER PUBLICATIONS

Searle, S. A., et al., "Breeding and Selection", Appendix I, *Chrysanthemums the Year Round,* Blandford Press, London, 1968, pp. 26–29, 320–327.

Gosling, S. G., "Appendix II Sporting and Irradiation", *The Chrysanthemum Manual,* Nat. Chrysanth. Soc. London, 1979, pp. 329–336.

*Primary Examiner*—James R. Feyrer

*Attorney, Agent, or Firm*—Foley & Lardner

[57] ABSTRACT

A Chrysanthemum plant named Dark Oreo particularly characterized by its flat capitulum form; daisy capitulum type; red-purple ray floret color; diameter across face of capitulum of up to 85 mm at maturity; uniform eight week photoperiodic flowering response to short days; peduncle length ranging from 10 to 15 cm on open, terminal sprays; short plant height when grown as a single stem spray cut mum; and excellent tolerance to low temperatures for bud initiation and flower development.

1 Drawing Sheet

The present invention comprises a new and distinct cultivar of Chrysanthemum, botanically known as *Dendranthema grandiflora,* and referred to by the cultivar name Dark Oreo.

Dark Oreo, identified as 83-486G03, is a product of a mutation induction program which had the objective of creating new Chrysanthemum cultivars that would expand the color range of an existing cultivar while retaining all other traits.

Dark Oreo was discovered and selected by Cornelis P. VandenBerg on Dec. 18, 1985 in a controlled environment in Salinas, Calif. as one flowering plant within a flowering block established as rooted cuttings from stock plants which had been exposed as unrooted cuttings to an X-ray source of 2000 rads. The irradiated parent was a mutation, which was delivered from an earlier irradiation of the cultivar identified as Oreo, disclosed in plant patent application Ser. No. 07/173,083, now U.S. Plant Pat. No. 6,882.

The first act of asexual reproduction of Dark Oreo was accomplished when vegetative cuttings were taken from the initial selection in March 1986 in a controlled environment in Salinas, Calif., by technicians working under formulations estabilshed and supervised by Cornelis P. VandenBerg.

Horticultural examination of controlled flowerings of successive plantings has shown that the unique combination of characteristics as herein disclosed for Dark Oreo are firmly fixed and are retained through successive generations of asexual reproduction.

Dark Oreo has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Dark Oreo, which, in combination, distinguish this Chrysanthemum as a new and distinct cultivar:

1. Flat capitulum form.
2. Daisy capitulum type.
3. Red-purple ray floret color.
4. Diameter across face of capitulum of up to 85 mm.
5. Uniform eight week photoperiodic flowering response to short days.
6. Peduncle length ranging from 10 to 15 cm on open, terminal sprays.
7. Short plant height, requiring two to three long day weeks prior to short days to attain a flowered plant height of 90 to 100 cm for year-round flowerings.
8. Excellent tolerance to low temperature for bud initiation and flower development.

The accompanying photographic drawing shows typical inflorescence and leaf characteristics of Dark Oreo, with the colors being as nearly true as possible with illustrations of this type. The color photograph is a perspective view of Dark Oreo grown as a single stem cut spray mum.

Of the commercial cultivars known to the inventor, the most similar in comparison to Dark Oreo are the parent cultivar Oreo. All traits of Dark Oreo and the induced mutation White Oreo, created through the same mutation induction program as Dark Oreo, and disclosed in applicant's pending application Ser. No. 07/436,821, filed simultaneously with the present application are similar to those of Oreo, except the color of the ray florets. The ray floret color of Dark Oreo is red-purple, compared with the light purple ray florets of Oreo. The cultivar White Oreo has white ray florets and greater vigor than both Dark Oreo and the parent cultivar Oreo.

In the following description color references are made to The Royal Horticultural Society Colour Chart. The color values were determined on plant material grown as a single stem cut spray mum in Salinas, Calif. on July 18, 1989.

Classification:

*Botanical.*—*Dendranthema grandiflora* cv Dark Oreo.

*Commercial.*—Daisy cut spray mum.

INFLORESCENCE

A. Capitulum:

*Form.*—Flat.

*Type.*—Daisy.

*Diameter across face.*—Up to 85 mm at maturity.

B. Corolla of ray florets:

*Color (general tonality from a distance of three meters).*—Red-purple.

*Color (upper surface).*—70B.

*Color (under surface).*—Closest to 75D, slightly tinged with 70B.

*Shape.*—Flat, oblong.

C. Corolla of disc florets:

*Color (mature).*—Closest to 14A.

*Color (immature).*—Closest to 144B.

D. Reproductive organs:

*Androecium.*—Present on disc florets only; moderate pollen.

*Gynoecium.*—Present on both ray and disc florets.

PLANT

A. General appearance:

*Height.*—Short; 90 to 100 cm as a single stem cut mum with two to three long day weeks prior to short days.

B. Foliage:

*Color (upper surface).*—147A.

*Color (under surface).*—147B.

*Shape.*—Deeply lobed and serrated.

I claim:

1. A new and distinct Chrysanthemum plant named Dark Oreo, as described and illustrated.

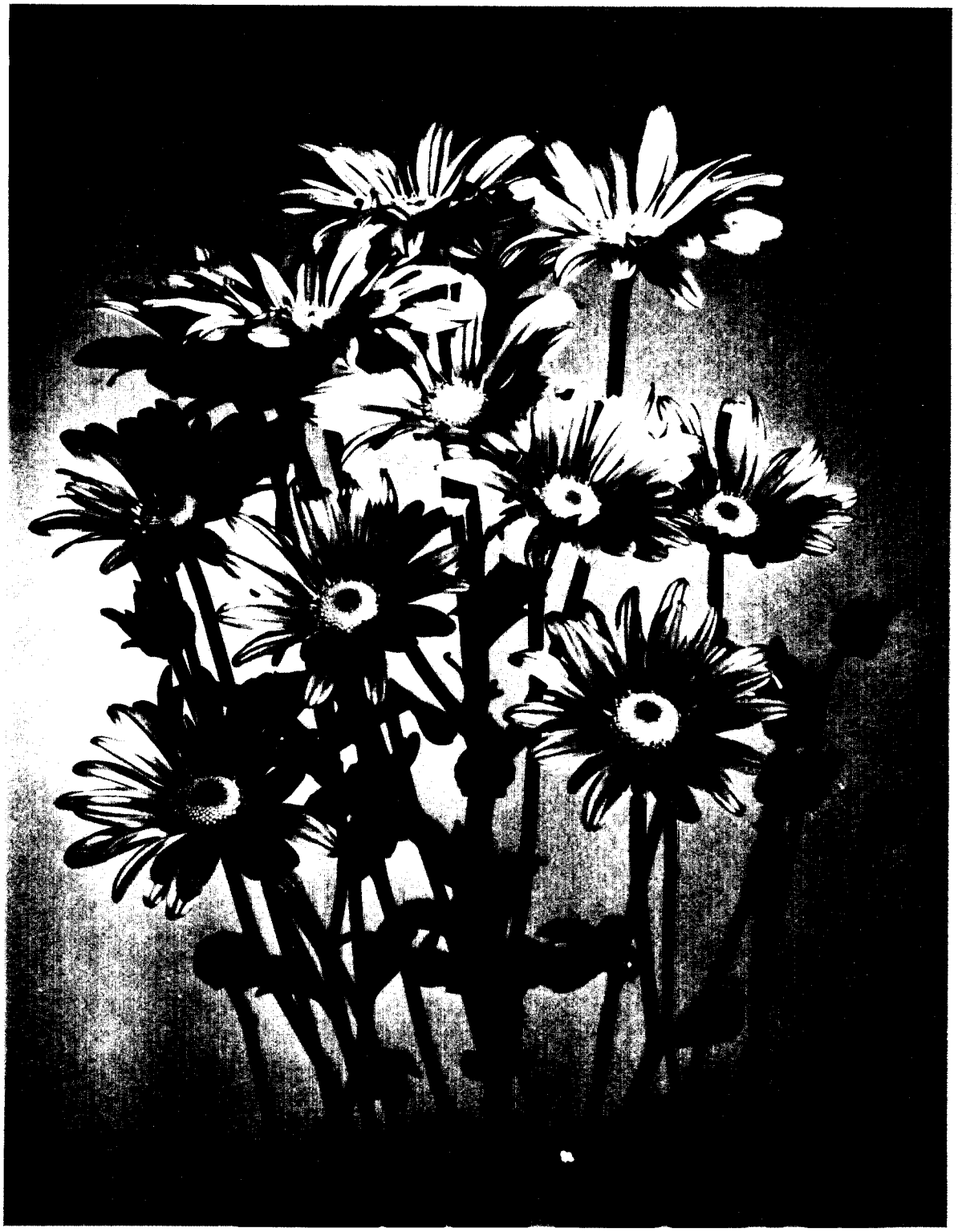

* * * * *